United States Patent [19]

Lucas et al.

[11] Patent Number: 5,288,424
[45] Date of Patent: Feb. 22, 1994

[54] THERMODYNAMIC MIXTURE OF ALKYL SUBSTITUTED BI(CYCLOHEXYLAMINE) ISOMERS

[75] Inventors: Peter A. Lucas, Allentown; Gamini A. Vedage, Bethlehem; Jeremiah P. Casey, Emmaus, all of Pa.

[73] Assignee: Air Products and Chemicals, Inc., Allentown, Pa.

[21] Appl. No.: 92,042

[22] Filed: Jul. 15, 1993

Related U.S. Application Data

[62] Division of Ser. No. 743,463, Aug. 9, 1991.

[51] Int. Cl.$^5$ ............................................. C08G 59/50
[52] U.S. Cl. ........................... 252/182.13; 525/504; 525/523; 528/122; 528/361; 528/407
[58] Field of Search ................. 252/182.13; 525/504, 525/523; 528/122, 361, 407

[56] References Cited

U.S. PATENT DOCUMENTS

| | | | |
|---|---|---|---|
| 2,817,644 | 12/1957 | Shokal et al. | 260/47 |
| 3,351,610 | 11/1967 | Preininger et al. | 260/47 |
| 3,427,282 | 2/1969 | Sundholm | 260/47 |
| 3,560,443 | 2/1971 | Sundholm | 260/47 |
| 3,629,181 | 7/1979 | Heer et al. | 260/31.8 |
| 4,293,687 | 10/1981 | Weissel et al. | 528/346 |
| 4,447,586 | 5/1984 | Shimp | 525/504 |
| 4,525,571 | 6/1985 | Burba et al. | 528/111 |
| 4,946,925 | 8/1990 | Strohmayer et al. | 528/122 |

FOREIGN PATENT DOCUMENTS 3-79625  4/1991  Japan.

*Primary Examiner*—Frederick Krass
*Attorney, Agent, or Firm*—Mary E. Bongiorno; James C. Simmons; William F. Marsh

[57] ABSTRACT

This invention pertains to alkyl substituted bi(cyclohexylamine) and derivatives having a high trans, trans-isomer distribution. This isomer distribution represents a thermodynamic mixture of the isomers and provides for extended pot life and extended thermal properties in epoxy resins which are not seen with the kinetic isomer mixture. The bridged cyclohexylamine and derivatives are represented by the formula:

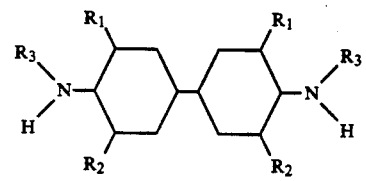

wherein;
$R^1$ is hydrogen or $C_{1-4}$ alkyl;
$R^2$ is $C_{1-4}$ alkyl; and
$R^3$ is hydrogen or $C_{1-4}$ alkyl The invention also relates to epoxy resins cured with the bridged bi(cyclohexylamines).

8 Claims, 2 Drawing Sheets

THERMODYNAMIC MIXTURE OF ALKYL SUBSTITUTED BI(CYCLOHEXYLAMINE) ISOMERS

This is a division of application Ser. No. 07/743,463 filed Aug. 9, 1991.

TECHNICAL FIELD

This invention pertains to bridged cycloaliphatic diamines for use in preparing epoxy resins and to the resulting epoxy resins.

BACKGROUND OF THE INVENTION

It is well known in the preparation of epoxide resins, which are generally glycidyl polyethers of polyhydric alcohols, that they can be cured by reacting with a polyamine. There is substantial literature available with respect to various types of amine curing agents for polyepoxide resin systems and representative literature include the following patents:

U.S. Pat. No. 2,817,644 discloses reacting polyepoxide resins with hydrogenated aromatic primary or secondary diamines where the aromatic amine has at least two amine hydrogens. Aromatic polyamines which are suited for hydrogenation include phenylenediamine, toluenediamine, 3,3'-diaminodiphenyl, p,p'-methylenedianiline and so fourth. The hydrogenated aromatic amines provide epoxy resin products having excellent hardness and excellent resistance to solvents and water.

U.S. Pat. Nos. 3,437,282 and 3,560,443 disclose the curing of epoxy resins with 4,4'-methylene-bis(2-alkylanilines) such as 4,4'-methylene-bis(2-ethylaniline) and 4,4'-methylene-bis(2-isopropylaniline). Utilization of these aromatic amine curing agents provide for extended pot life in epoxy resins relative to methylenedi(aniline). The '443 patent discloses a variation to the '282 disclosure in that epoxy resins are cured with the 4,4'-methylene-bis(2-alkyl-6-methylaniline) derivatives. In contrast to the '282 patent the amine in the '443 patent is a dialkyl substituted bridged aromatic amine having alkyl groups in each ortho position to each amine group. The '443 curing agents provide for extended pot life and yet provide epoxy resins having a good heat distortion temperatures.

U.S. Pat. No. 3,351,610 discloses the use of di-tertiary alkylene-bis(cyclohexylamines) which include 2,2-bis(4-dimethylaminocyclohexyl)propane and bis(4-dimethylaminocyclohexyl)methane as curing catalysts. In contrast to prior art tertiary amines, they provide epoxy resins having good mechanical properties in terms of flexural strength, impact strength, etc. Prior to this development it was customary to use primary and secondary amines where the amines would react with the epoxy resin for crosslinking.

U.S. Pat. No. 3,629,181 discloses adducts of polyepoxide resins and cycloaliphatic or cycloaliphatic-aliphatic di-primary diamines. Cycloaliphatic di-primary amines suited for adduct formation include diaminocyclohexanes and bridged cyclohexylamines where the bridge is a methylene or a propylidene group and representative compounds include 2,2-di(4-aminocyclohexyl)propane and 4,4'-methylene-bis(2-methylcyclohexylamine). Also included is 3-aminomethyl-3,5,5-trimethyl-1-cyclohexylamine or isophoronediamine as it is sometimes called.

U.S. Pat. No. 4,525,571 discloses the formation of surface coatings comprising epoxy resins and amine curing agents such as a cycloaliphatic di-primary amines, e.g. 1,2-diaminocyclohexane.

U.S. Pat. No. 4,293,687 discloses various tetraalkylated bis(cyclohexylamine) derivatives which include bis(3,5-dimethyl-4-aminocyclohexyl)methane and bis(3,5-diethyl-4-aminocyclohexyl)methane. These bridged cyclohexylamine derivatives are suggested as being suited as valuable intermediate products for the production of polycondensation resins and lacquers. Representative condensation resins include polyurethanes and polyamides.

U.S. Pat. No. 4,946,925 discloses various bridged bi(cyclohexylamine) derivatives as curing agents. Each cyclohexylamine group has two alkyl groups where the alkyl groups are in the 2 and the 5 position and the main groups are in the 4 position. Specific curing agents include 2,2',5,5'-tetramethylmethylenedi(cyclohexylamine). The tetraalkyl substitution pattern in a bridged cyclohexylamine derivative provides for extended pot life by retarding activity of the amine as a curative and the tetraalkyl substitution also enhances thermal properties of the epoxy resin.

SUMMARY OF THE INVENTION

This invention pertains to alkyl substituted bi(cyclohexylamines) bridged by a single bond having a high trans, trans-isomer distribution. This isomer distribution represents a thermodynamic mixture of the isomers and provides for excellent pot life and thermal properties in epoxy resins which are not seen with the kinetic isomer mixture. By thermodynamic mixture it is meant that at least 40%, preferably 50%, of the isomer mixture is in the EE form, that is, the 3-position R group and 4-position amine group are both equatorial when the ring bridge is equatorial. The 4-position amine and ring bridge are trans. The bridged cyclohexylamine derivatives are represented by the formula:

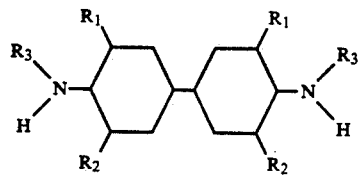

wherein:

$R^1$ is hydrogen or $C_{1-4}$ alkyl;
$R^2$ is $C_{1-4}$ alkyl; and
$R^3$ is hydrogen or $C_{1-4}$ alkyl Several advantages are associated with the bridged bi(cyclohexylamine) and derivatives of this invention and these advantages include:

1. extended pot life of the epoxide resin permitting flexibility in formulation.
2. enhanced thermal stability of polyepoxy resins cured with the bridged cyclohexylamine derivatives;

DETAILED DESCRIPTION OF THE INVENTION

Figure 1:
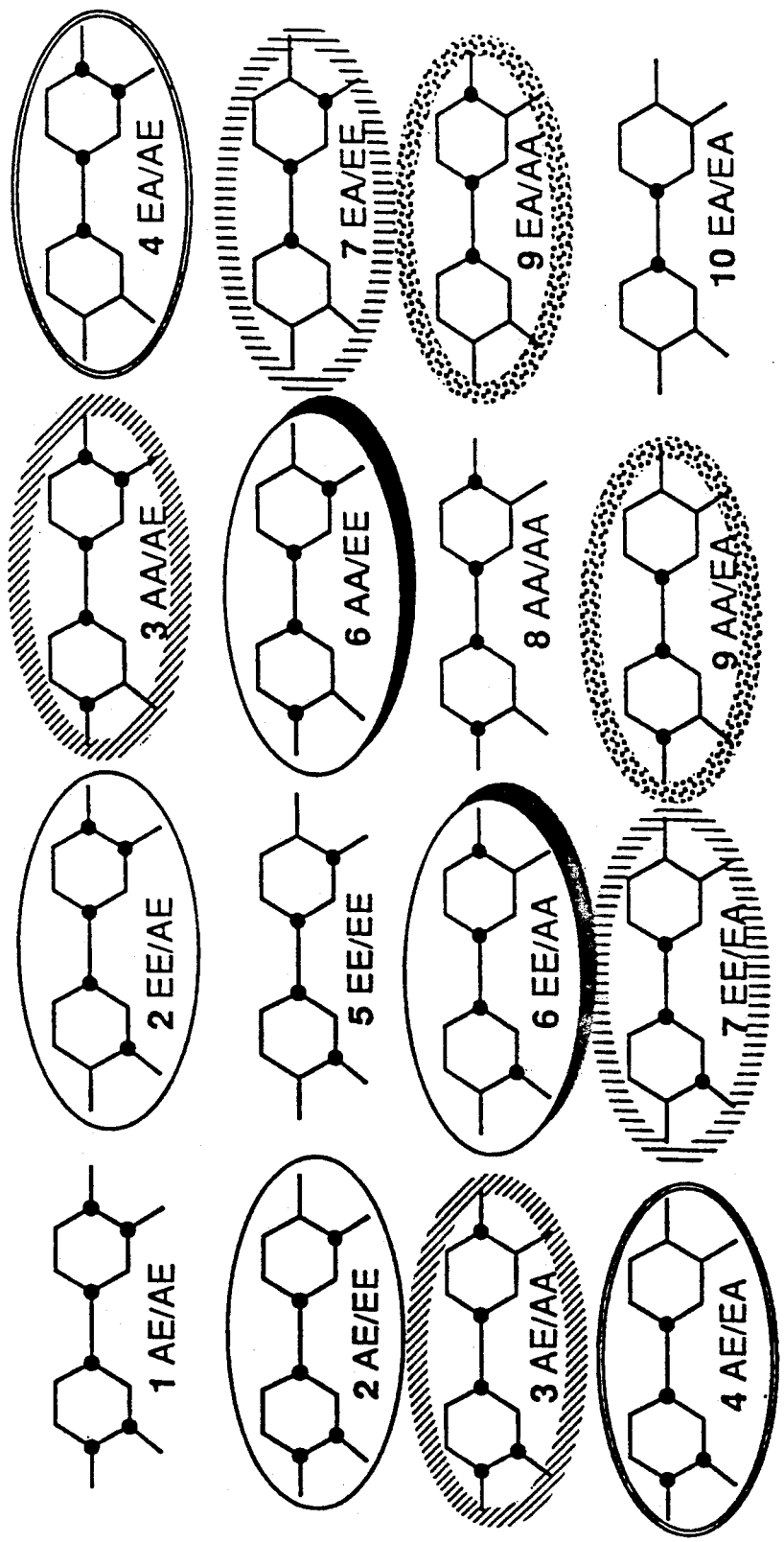
FIG. 1 is a view providing structural formula of unique isomers obtained on the hydrogenation of o-tolidine.

The polyepoxide resins which can be cured using the thermodynamic mixture of alkyl substituted bi(cyclohexylamine) isomers and derivatives of this invention include those polyepoxides having more than one epoxy group per molecule with the epoxy group typically being a terminal 1,2-epoxy group. The resins are well known and representative resins are described in U.S. Pat. No. 3,351,610, 4,447,586 and 4,946,925 which are incorporated by reference. Although both liquid and solid epoxy resins can be used, polyepoxide resins which are liquid are preferred. Examples of polyepoxide resins which are conventionally used include those which are based upon aromatic phenols and aliphatic polyols. Representative aromatic phenolic polyepoxides typically used include glycidyl polyethers of polyhydric phenols derived from a polyhydric phenol and epihalohydrin. The resulting epoxy resin generally will have an epoxide equivalent weight ranging from about 100 to 1,000. Epihalohydrin used in preparing the polyepoxide resins include epichlorohydrin and epibromohydrin and polyhydric phenols include resorcinol, hydroquinone, p,p'-dihydroxydiphenylmethane; p,p'-dihydroxydiphenylpropane or bisphenol A as it is sometimes called. Of these polyhydric phenols, those based upon bisphenol A are the most common and preferred in the practice of this invention.

Cycloaliphatic epoxide resins such as vinylcyclohexene dioxide; 3',4'-epoxy-cyclohexylmethyl-3,4-epoxycyclohexane carboxylate and liquid polyglycidyl ethers of polyalcohols such as 1,4-butanediol or polypropylene glycol can also be used as the epoxide resin.

Other types of polyepoxide resins which can be cured with the bridged bi(cyclohexylamine) derivatives are glycidyl polyester resins which are prepared by reacting an epihalohydrin with an aromatic or aliphatic polycarboxylic acid. In addition, polyepoxide resins where the glycidyl functionality is a glycidyl amine prepared by reacting a polyamine with an epichlorhydrin can also be used.

The bridged cyclohexylamine derivatives used for curing polyepoxide resins are represented by the formula:

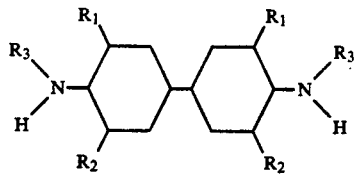

wherein
R$^1$ is hydrogen or C$_{1-4}$ alkyl; R$^2$ is C$_{1-4}$ alkyl and R$^3$ is hydrogen or C$_{1-4}$ alkyl.

In addition, the bridged bi(cyclohexylamine) derivatives utilized present as a thermodynamic isomer mixture, i.e. a substantial proportion, e.g. greater than about 40% of the isomer mixture is in the trans, trans-isomer configuration. When less than 40% of the isomer mixture, generally less than 50%, is in the thermodynamic form, physical properties may deteriorate somewhat.

Differentiation of the thermodynamic isomer mixture from the kinetic isomer mixture can be based on the resulting isomer configuration. Using methylenedi(cyclohexylamine) (MDCHA) as a guide, when each ring has two chiral centers, the potential isomers are cis/cis, cis/trans, trans/cis and trans/trans. Due to the plane of symmetry in MDCHA the cis/trans and trans/cis isomers are equivalent, resulting in three isomers.

In 3,3'-dimethylmethylenedi(cyclohexylamine) (DMMDCHA) and 3,3'-dimethylbi(cyclohexylamine) (DMBCHA) there are three chiral centers in each ring, and no plane of symmetry in the molecule. Within each ring the isomer combinations for the 1,2 and 4 position substituents are again four in number (c/c c/t t/c and t/t). Statistically, with 6 chiral centers, there are 2$^6$ or 64 possible isomers; they are as follows:

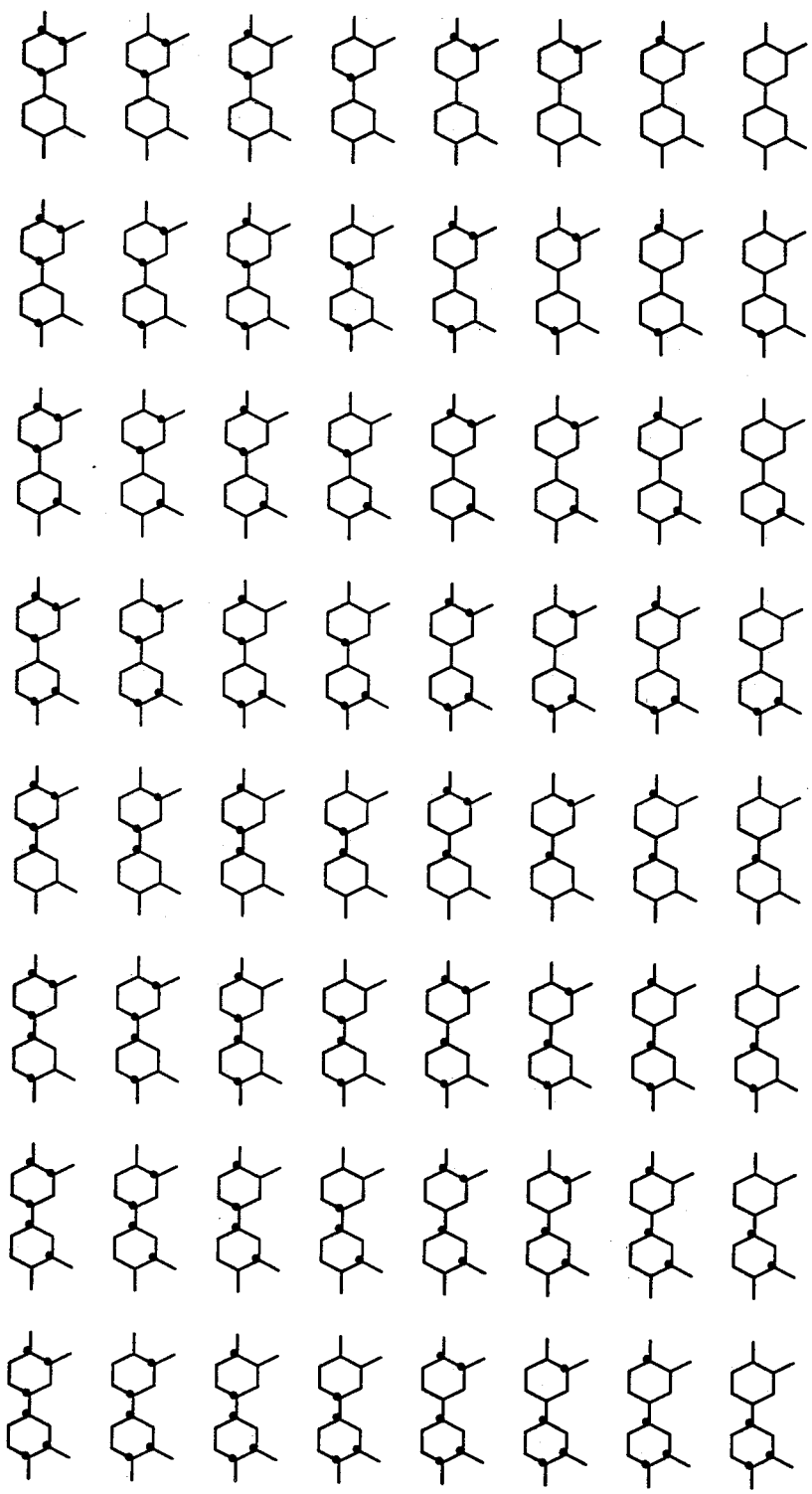

On review of the isomer structures it will be noted that the isomers in the lower right quadrant are superimposable on those in the upper left by reflection through the mirror plane of the page, as are those in the lower left upon those in the upper right. The upper left and upper right quadrants each are composed of 16 isomers possible in DMBCHA or DMMDCHA. The upper left quadrant isomers all have both ring bridge protons placed above the plane of the page; those isomers in the upper right have one ring bridge proton below and above the plane of the page. Further analysis reveals redundancy by mirror plane reflection about the long axis of the molecule to give ten unique isomers within each of the remaining two quadrants; the six pairs which are redundant in the upper left quadrant are similarly circled: Also, there are 10 unique isomers in the upper right quadrant for a total of 20. FIG. 1 illustrates these unique isomers.

Although not intending to be bound by theory, it is believed that the high trans/trans- amine-ring bridge-amine 'linear' configuration in the final product combined with close-packing about the ring bridge itself in the thermodynamic isomer mixture provides for enhanced properties. The kinetic isomer mixture does not have this same close packing nor does the corresponding homologue MDCHA (PACM) and substituted derivative DMMDCHA. It is also speculated that same close ring bridge packing is the reason more forcing hydrogenation conditions are required to attain the thermodynamic equilibrium mixture of the DMBCHA isomer relative to those of MDCHA (PACM) and DMMDCHA.

The bridged bi(cyclohexylamine) derivatives can be synthesized in conventional manner followed by hydrogenation under extreme conditions to effect isomerization of the isomers for generating a reaction mixture high in the trans, trans-isomer configuration. Hydrogenation of the bridged bi(cyclohexylamine) derivatives generally must be carried out under rigorous conditions using a catalyst which is sufficiently effective for isomerizing the reaction mixture to a product which has a high trans,trans-isomer configuration in the respective compounds. Typically a ruthenium catalyst is used to effect hydrogenation and conditions of hydrogenation will range from a hydrogen pressure of from 500 to 4500 psig, temperatures ranging from 150° C. to 250° C. and reaction times may extend from a period of 1 to 24 hours. Monitoring of the hydrogenation process by sampling is the best method of determining when the hydrogenation is complete with respect to generating the required level of reaction product having the trans,-trans-isomer configuration. Hydrogenation of the bridged bi(cyclohexylamines) under less rigorous conditions generates a kinetic isomer mixture and these derivatives, although suited for curing epoxy resins, do not afford the significant benefits in terms of properties in the resulting epoxy resin offered by the thermodynamic mixture.

Representative examples of the bridged bi(cyclohexylamines) include 2,2'-dimethylbi(cyclohexylamine); 2,2'-diethylbi(cyclohexylamine); 2,2'-diisopropylbi(cyclohexylamine); 2,2'-dimethyl-N,N'-dimethybi(cyclohexylamine); 2,2',4,4'-tetramethylbi(cyclohexylamine); 2,2'-dimethyl-4,4'-diethylbi(cyclohexylamine) and 2,2'-dimethyl-4,4'-diisopropylbi(cyclohexylamine).

The polyepoxide resin can be cured in conventional manner by effecting reaction with the bridged cyclohexylamine derivatives. Typically the amount of bridged bi(cyclohexylamine) derivative which is reacted with the polyepoxide resin will range from a level of 0.6 to 1.5 times the stoichiometric or equivalent amount of polyepoxide resin and preferably the level of bridged bi(cyclohexylamine) derivative to epoxy resin is from about 0.9 to 1.0 times the stoichiometric amount, stoichiometric being two equivalents epoxide per equivalent amine.

Conventional epoxide resins, plasticizers, fillers, pigments, solvents, etc. used in formulating coatings, mold compositions, lacquers, etc. can be used and selection is at the option of the formulator. The adjustment of cure temperatures and curing times for polyepoxide resins is within the discretion of the formulator. Representative accelerators which may be used, although not mandatory, include: boron trifluoride, amine complexes and metal fluoroborate systems, e.g. copper fluoroborate.

The following examples are intended to illustrate various embodiments of the invention and are not intended to restrict the scope thereof.

EXAMPLE 1

Preparation of 3,3'-Dimethylbi(cyclohexylamine) (DMBCHA) Using Ruthenium Catalyst Orthotolidine, 212.3 g (1.0 mole Fluka anhydrous), dissolved in 637 ml tetrahydrofuran (THF) was placed in a 2 liter autoclave. 8.49 g of a 5% Ru on alumina catalyst from Engelhard was added followed by addition of 2.1 g anhydrous lithium hydroxide base promoter. The reaction was sealed, purged three times with nitrogen, then twice with hydrogen before being pressurized with hydrogen, to 1500 psi. The reaction mixture was brought to 165°-180° C. while maintaining 750 rpm sealed stirrer agitation. The reactor content then were held at that temperature to effect reduction. At reaction temperature the reactor pressure was brought to 1900 psi and allowed to drop to no lower than 1500 psi before being recharged to 2500 psi. When slightly greater than stoichiometric hydrogen consumption had occurred (89 min), the reaction mixture was cooled, vented, and purged with nitrogen. The crude reaction solution was removed from the autoclave, filtered free of catalyst, and analyzed by capillary chromatography. Product DMBCHA isomers comprised 95.5% of the reaction crudes and were analyzed by capillary flame ionization detection. Deaminates were 4.5%.

EXAMPLE 2

Preparation of 3,3'-Dimethylbi(cyclohexylamine) (DMBCHA) Using Rhodium on Alumina Catalyst The procedure of Example 1 was essentially repeated except that an alternative catalyst was used. In this example 212.3 g (1.5 moles) orthotolidine was dissolved in 637 ml THF and placed in the autoclave. 8.49 g of 5% Rh on alumina catalyst from Engelhard and 2.3 g anhydrous LiOH were added. The reactor was purged thrice with nitrogen, thrice with hydrogen, then vented to atmospheric pressure. The reactor then was pressurized with to 1500 psi and The stirred reaction mass was brought to 165°-180° C. Reactor pressure was maintained between 2290 and 1500 psi as hydrogen uptake rate was monitored. When slightly greater than stoichiometric hydrogen uptake was reached (60 min), the reactor was cooled, vented and purged. Crude DMBCHA product was 90.2%. Deaminates were 8.7% and single ring reduced coproduct 1.1%.

EXAMPLE 3

Preparation of 3,3'-Dimethylbi(cyclohexylamine) (DMBCHA) Using Rhodium on Titania Catalyst The procedure of Example 1 was followed except that a Rh on titania catalyst was used for orthotolidine hydrogenation after in-situ catalyst reduction. More specifically, 3.03 g of a 5% Rh on titania catalyst from Engelhard and 750 ml THF were charged to a 2 L autoclave equipped with an in-line 5 micron frit cartridge filter on an external port. The reactor was purged thrice with nitrogen, thrice with hydrogen, then vented to atmospheric pressure before hydrogen pressurization to 1000 psi. The stirred reaction mass was brought to 200° C. reaction temperature. Reactor pressure was maintained between 1000 and 900 psi for 3 hours before cooldown. The reactor was pressurized to 50 psi with nitrogen and the solvent filtered from the catalyst. The catalyst was backflushed with 637 ml THF that was then removed under pressure, and the reactor was charged with 212.3 g orthotolidine in 637 ml THF. No alkali promoter was used. Ring reduction after nitrogen and hydrogen purging was accomplished in 86 minutes at 165°-180° C. and 2260-1500 psi. Deaminates were 7.9%; half reduced coproduct was 4.2%. Although no alkali promoter was used, the amount of reduced coproduct was only slightly higher than was achieved with the alkali promoted rhodium on aluminum catalyst in Example 2.

EXAMPLE 4

Preparation of 3,3'-Dimethylbi(cyclohexylamine) (DMBCHA) Using Ruthenium on Titania Catalyst Reduction of orthotolidine was effected using 5% Ru on titania (Engelhard) 106 g aromatic diamine was dissolved in 530 ml THF (5:1 vol:wt versus 3:1 vol:wt as in prior examples) and charged to the 2 L autoclave with 4.25 g catalyst. The reactor was purged thrice with nitrogen, thrice with hydrogen, then vented to atmospheric pressure before hydrogen pressurization to 2000 psi. The reaction was complete in 120 minutes at 2700-2000 psi hydrogen pressure and 170°-185° C. There was complete ring reduction; desired product was 96.8%, deaminates were 3.2% when measured by capillary gas chromatography. As can be learned from Example 3, ruthenium is not as effective as rhodium for effecting the initial hydrogenation.

EXAMPLE 5

Preparation of 3,3'-Dimethylbi(cyclohexylamine) (DMBCHA) Using Rhodium on Titania Catalyst (50% Diamine)

The procedure of Example 1 was followed except that the reduction of orthotolidine was effected using 5% Rh on titania (Engelhard) admixed with 5% Pd on alumina. (Rh:Pd 1:1) At 850 psi, 192° C. the reduction of a solution of 50% diamine in THF was complete in 85 minutes using 3% catalyst by weight relative to diamine. DMBCHA yield was 89% with 11% deaminates. There was complete ring reduction.

EXAMPLE 6

Preparation of 3,3'-Dimethylbi(cyclohexylamine) (DMBCHA) Using Rhodium on Titania Catalyst at 35% Diamine The procedure of Ex 5 was followed except that the feedstock comprised a 35% solution of orthotolidine. At 35% diamine in THF solvent results at 85 minutes were comparable, 88% product with 12% deamination coproducts. The reaction time also compared favorably with the rhodium catalyst which was used in Example 3.

EXAMPLE 7

Confirmation of Isomer Peaks

The hydrogenation products generated in Examples 1-4 were analyzed and found to have multiple resolved peaks by extended elution profile capillary chromatography. These peaks were confirmed as DMBCHA by mass spectrometry. Isomer distribution varied only slightly as a function of run conditions such as catalyst, temperature, promoter addition and hydrogen pressure at the point of reaction completion. For Examples 1-4 the 8 major resolved isomer peaks, normalized amidst others to 100% DMBCHA composition, varied as given below:

|   | Isomer peak | | | | | | | |
|---|---|---|---|---|---|---|---|---|
|   | pk 1 | pk 2 | pk 3 | pk 4 | pk 5 | pk 6 | pk 7 | pk 8 |
| Run 1 - Ru/Al | 3.2 | 3.0 | nr | 17.7* | 37.2 | 23.0 | 5.6 | 8.6 |
| Run 2 - Rh/Al | 1.1 | 1.0 | 3.4 | 5.0 | 23.9 | 41.3 | 5.4 | 15.9 |
| Run 3 - Rh/Ti | 1.0 | .9 | 3.0 | 4.1 | 25.0 | 33.7 | 8.3 | 19.1 |
| Run 4 - Ru/Ti | 1.7 | 1.6 | nr | 10.1* | 40.5 | 29.9 | 5.4 | 9.1 | nr indicates not resolved,
*indicates summed integration with prior non-resolved peak.

For Examples 5 and 6 the 5 major isomer peaks were resolved under less extended capillary run conditions normalized among themselves to 100%, were:

|   |   | Isomer peak | | | | |
|---|---|---|---|---|---|---|
|   |   | pk 4 | pk 5 | pk 6 | pk 7 | pk 8 |
| Ex 5 | Rh/Ti, Pd/Al | 7.5 | 27.4 | 34.7 | 9.7 | 20.7 |
| Ex 6 | Rh/Ti, Pd/Al | 12.1 | 30.5 | 30.1 | 10.1 | 17.1 |

EXAMPLE 8

Isomerization of DMBCHA to Thermodynamic Isomer Mixture

A portion of the DMBCHA product obtained in Example 5 using the catalyst of Rh/TiO$_2$/Pd/Al$_2$O$_3$ was placed in a one gallon autoclave with 3 wt % (based on diamine) of Ru on alumina catalyst promoted with 0.3 wt % lithium hydroxide. After normal nitrogen purging followed by hydrogen pressurization, mixing and venting without mixing, post-reduction isomerization of the DMBCHA was conducted at 195° C. and 850 psi H$_2$ pressure. The product DMBCHA isomers after 10 hours of contact time were:

|   | Isomer peak | | | | |
|---|---|---|---|---|---|
|   | pk 4 | pk 5 | pk 6 | pk 7 | pk 8 |
| Run 7 - Ru/Al$_2$O$_3$ | 48.7 | 25.4 | 5.3 | 15.8 | 4.7 |

The product was analyzed and deaminates increased from 11.2 to 15.9%, the secondary amine went from non-observable to 1.9% as DMBCHA composition in the organic phase fell from 88.8% after Example 5 to 82.2% after this Example 8. A review of the isomer peak data shows an increase in the amount of isomer at peak 4 and 7 and a decrease in 6 and 8. As a qualitative measurement the shift in components to peaks 4 and 7 and the decrease in peaks 6 and 8 indicate a compositional difference in the thermodynamic mixture from that of the kinetic mixture.

EXAMPLE 9

Isomerization of DMBCHA to Thermodynamic Isomer Mixture

A portion of the DMBCHA product obtained in Example 6 from Rh/TiO$_2$/Pd/Al$_2$O$_3$ reduction was dissolved to 35% in THF and placed in an autoclave with 3 wt % (based on diamine) of Ru on alumina catalyst. After normal nitrogen purging, then hydrogen pressurization, mixing and venting without mixing, post-reduction isomerization was conducted at 192° C. and 850 psi H$_2$ pressure. Samples were withdrawn over time were analyzed for DMBCHA, deaminates and secondary amine condensation product:

| TIME (min) | % DMBCHA | Deaminates | 2° amines | pk 4 | pk 5 | pk 6 | pk 7 | pk 8 |
|---|---|---|---|---|---|---|---|---|
| 0 | 87 | 12 | 0.5 | 12.4 | 26.0 | 26.5 | 13.0 | 22.1 |
| 60 | 87 | 12 | 0.5 | 27.3 | 29.9 | 17.7 | 12.7 | 12.3 |
| 100 | 87 | 12 | 0.9 | 35.3 | 29.8 | 10.6 | 15.8 | 8.5 |
| 340 | 86 | 12 | 1.7 | 43.8 | 26.1 | 5.5 | 18.5 | 6.1 |
| 640 | 86 | 12 | 1.7 | 50.5 | 22.2 | 3.5 | 19.2 | 4.6 |

Only slight (<2%) secondary amine was formed as the isomer composition changed greatly to give the same thermodynamic isomer mixture as previously attained only by extended post treatment.

EXAMPLE 10

Isomerization of DMBCHA to Thermodynamic Isomer Mixture

A portion of the DMBCHA product obtained from Rh/TiO$_2$/Pd/Al$_2$O$_3$ reduction of 30% o-tolidine in THF at 192° C. and 850 psi H$_2$ pressure and placed in an autoclave with 3 wt % (based on diamine) of Ru on alumina catalyst. After normal nitrogen, then hydrogen pressurization, mixing and venting without mixing, post-reduction isomerization was conducted at 195° C. and 850 psi H$_2$ pressure. Samples were withdrawn after 15 hours and analyzed for DMBCHA isomer composition; these samples were found to attain the thermodynamic equilibrium mixture as evidenced by equivalence to the ultimate product in Example 9 and were isolated by solvent removal and distillation following catalyst removal.

| | Isomer peak | | | | |
|---|---|---|---|---|---|
| | pk 4 | pk 5 | pk 6 | pk 7 | pk 8 |
| Run 9 start- | 7.7 | 20.9 | 39.2 | 8.9 | 23.4 |
| Run 9 - Ru/Al$_2$O$_3$ | 49.6 | 24.2 | 4.0 | 17.6 | 4.7 |

Note the shift in isomer composition in pk 4, 6, 7 and 8.

EXAMPLE 11

DMBCHA Product Purification

The reaction product of Example 4 to 10 was distilled through a 10" Vigreaux column from a 2 L round bottom flask, DMBCHA product aliphatic diamine was collected at 205°–210° C. under 55–60 mm of Hg pressure. Using a 1"×12" packed column (0.16" stainless steel Propak) aliphatic diamine isomer mixtures were distilled at 214°–216° C. at 2 mm of Hg and showed negligible isomer separation at 1:1 reflux ratio.

EXAMPLE 12

Dimethylmethylenedi(cyclohexylamine) (DMMDCHA) Analogue Preparation 3,3'-Dimethylmethylenedi(aniline) (DMMDA) was hydrogenated in a procedure similar to Example 2 to 3,3'-dimethylmethylenedi(cyclohexylamine) (DMMDCHA) using a Rh/Ti catalyst to give the kinetic mixture of isomers and using Ru/Al$_2$O$_3$ to give the thermodynamic dynamic equilibrium mixture of isomers. Unlike DMBCHA, DMMDCHA yields the thermodynamic mixture of isomers directly upon Ru reduction, requiring no post treatment. Capillary GC isomer distribution was:

| | Isomer peak | | | | |
|---|---|---|---|---|---|
| | pk 1 | pk 2 | pk 3 | pk 4 | pk 5 |
| Rh/Ti- start | 5.6 | 28.1 | 39.4 | 7.4 | 19.5 |
| Ru/Al$_2$O$_3$ isomerized | 38.0 | 38.1 | 7.8 | 10.9 | 5.4 |

It is believed that because of the increased flexibility and rotatability of the DMMDCHA about the methylene bridge less forcing conditions are required to obtain the thermodynamic mixture from the kinetic mixture.

EXAMPLE 14

Isomer-Combinatorial Identification & Quantitative Analysis

Analysis of isomer mixtures of Ex 5, 10 and 13 was done by heteronuclear two-dimensional NMR. Isomer quantitation was limited to a ring combinatorial identification, not being able to distinguish

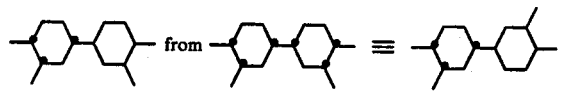

due to the lack of through-ring 3- and 3'-position methyl group substituent differences. In DMMDCHA there is very free rotation about the methylene group ring bridge and no indication of the above discrimination. In DMBCHA only some slight 13C NMR discrimination is noted as slight peak splitting at 300 MHz. The ring combinatorial identification is most easily presented by analysis of each ring described by the conformation of the amine and methyl groups as either axial (A) or equatorial (E) in each ring relative to an equatorial bridging group. Data below are for the kinetic isomer mixture of DMBCHA.

| Kinetic Isomer Mixture of DMBCHA | | | | | |
|---|---|---|---|---|---|
| single ring NMR analysis, % | EE 25.98 | AA 9.44 | EA 16.24 | AE 48.34 | |
| EE | 25.98 | 6.75 | 2.45 | 4.22 | 12.56 |
| AA | 9.44 | 2.45 | 0.89 | 1.53 | 4.56 |
| EA | 16.24 | 4.22 | 1.53 | 2.64 | 7.85 |
| AE | 48.34 | 12.56 | 4.56 | 7.85 | 23.37 |

Again a collapse from 16 possible to 10 distinct isomers due to the equivalence of, for instance, the isomers EExAA and AAxEE (2.45+2.45=4.90%) facilitates comparison among the products of hydrogenation.

| NMR | Isomer | Kinetic DMBCHA-K | Thermodynamic DMBCHA-T | Kinetic DMMDCHA-K | Thermodynamic DMMDCHA-T |
|---|---|---|---|---|---|
| EE | EE | 6.75 | 33.73 | 7.68 | 42.75 |
| EE | AA | 4.90 | 12.40 | 5.14 | 15.84 |
| EE | EA | 8.44 | 11.14 | 6.36 | 7.90 |
| EE | AE | 25.12 | 25.14 | 28.56 | 21.52 |
| AA | AA | 0.89 | 1.14 | .86 | 1.47 |
| AA | EA | 3.06 | 2.04 | 2.14 | 1.46 |
| AA | AE | 9.12 | 4.62 | 9.58 | 4.00 |
| EA | EA | 2.64 | .92 | 1.31 | .37 |
| EA | AE | 15.70 | 4.16 | 11.82 | 1.98 |
| AE | AE | 23.37 | 4.69 | 6.55 | 2.71 |

Figure 2:
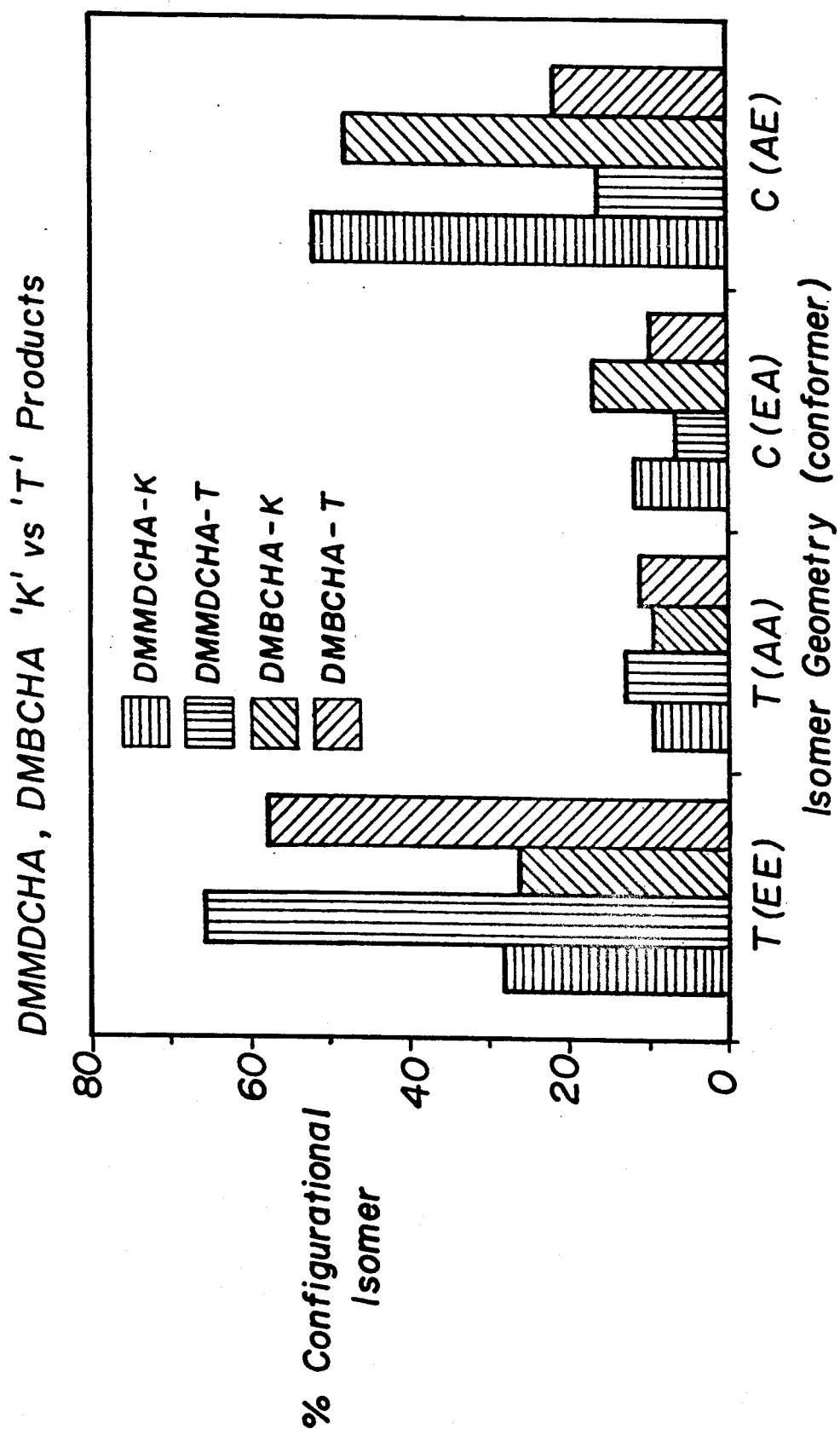
FIG. 2 is a graphical presentation of the % configurational isomer versus isomer geometry for hydrogenated o-tolidine and related compounds.

The match against capillary GC isomer peaks is consistent with interpretation of the hydrogenation results as first generating cis amine/bridge ring products which isomerize under changed catalyst and process conditions to trans products. FIG. 2 is a graphical view of the percent configurational isomers versus isomer geometry. It shows the high level of trans (EE) contained in the thermodynamic mixture of hydrogenated o-tolidine.

EXAMPLE 15

Gel Time for Epoxy resins

The instrument used to demonstrate reaction time in epoxy resin/amine curing formulations was a Sunshine ® Gel Time Meter. The principle of operation is based on a circuit disconnect once a rotating glass rod reaches a specific torque. This torque is characteristic of a torsion spring of constant dimensions connected between the rod and the instrument. The rod is immersed in the resin/curing agent formulation held in a test tube and the test tube suspended in a constant temperature bath.

Formulations were prepared to determine reactivity profile in a glass container. The formulation consisted of the following:

100 parts by weight of the diglycidyl ether of Bisphenol A having an epoxide equivalent weight of 187,
30.2 parts by weight of DMBCHA or
28.3 parts by weight of PACM or (MDCHA) or
32.1 parts of DMMDCHA The level of addition of the kinetic and thermodynamic mixture of isomers of dimethylbi(cyclohexylamine), DMBCHA-K and DMBCHA K was based on an amine hydrogen equivalent weight (AHEW) of 56.1. PACM refers to 4,4-methylenedi(cyclohexylamine). Numbers 20 and 48 refer to 20 and 40% trans, trans-isomer content in the PACM composition respectively.

Each mixture was stirred at room temperature (22° C.) until homogeneous but no longer than five (5) minutes. A portion of each mixture (10 g) was placed in the test tube used for the gel meter described above. The gel timer glass rod was placed into the mixture and the test tube secured in a water bath preheated to 60° C. The glass rod was attached to the instrument and aligned so the rotating rod would not touch the sides of the test tube. The gel timer was turned on and allowed to run until a gel time was registered. The resultant gel times at 60° C. are:

| | DMBCHA-K | DMBCHA-T | DMMDCHA-K | DMMDCHA-T | PACM-20 | PACM-48 |
|---|---|---|---|---|---|---|
| Gel Time (minutes) @ 60° C. | 53 | 69 | 52 | 52 | 23 | 26 |

The delayed reactivity of DMBCHA, both kinetic and thermodynamic, relative to PACM is similar to that of the similarly sterically hindered DMMDCHA to that of PACM. What is surprising is the much longer gel time noted for the thermodynamic mixture of DMBCHA, i.e. DMBCHA-T relative to the kinetic mixture of isomers, 69 versus 53 minutes at 60° C. No such difference is noted at 60° C. for the DMMDCHA K and T isomer mixtures; both recorded times of 52 minutes.

EXAMPLE 16

Epoxy Reactivity

Exotherm profiles of the formulation for the thermodynamic and kinetic isomer mixtures of DMBCHA were observed using a differential scanning calorimeter (DSC). After each sample was mixed, it was immediately weighed into a DSC sample pan on an analytical balance and placed in the DSC cell of a DuPont 9900 thermal analyzer. The cell was preprogrammed to increase in temperature from 23° C. to 250° C. at a rate of 10° C./minute. Analysis of the resulting exotherms for each formulation indicates a shift in the location of the peak exotherm for the slower reactivity formulations. Comparisons were made against PACM isomers.

| DSC Reactivity Profile | | | | | | |
|---|---|---|---|---|---|---|
| Profile | DMBCHA-K | DMBCHA-T | DMMDCHA-K | DMMDCHA-T | PACM-20 | PACM-48 |
| Onset (°C.) | 92 | 96 | 92 | 92 | 86 | 86 |
| Peak (°C.) | 124 | 124 | 125 | 124 | 112 | 112 |
| ΔH (J/g) | 280 | 294 | 278 | 354 | 395 | 395 |

Again the delayed reactivity of the sterically hindered aliphatic diamines DMBCHA and DMMDCHA relative to MDCHA (PACM) is demonstrated. The thermodynamic mixture of DMBCHA-T gave delayed reactivity compared to DMBCHA-K.

EXAMPLE 17

Epoxy Resin Physical Properties

To demonstrate the epoxy performance of the compositions of this invention, samples were prepared for physical property testing. Their composition and mix procedure were identical to those in Examples 5 and 9. Each sample was degassed prior to pouring ⅛" thick castings. The castings were gelled and post cured 2 hours at 80° C. followed by 3 hours at 150° C. Glass transition temperatures (Tg) were run on the cured castings to determine the extent of cure. A differential scanning calorimeter was used, programmed with a 10° C./minute rate of increase from 23° C. to 250° C. Upon completion of the scan, the sample was cooled to 23° C. in the DSC cell using a dry ice cold finger and a second scan was run under identical conditions. The Tg for each sample is reported from the second scan.

| Thermal Properties | | | | | | |
|---|---|---|---|---|---|---|
| | DMBCHA-K | DMBCHA-T | DMMDCHA-K | DMMDCHA-T | PACM-20 | PACM-48 |
| Tg (°C.) | 160 | 178 | | | 161 | 166 |
| E' (°C.) | 140 | 162 | 138 | 143 | 152 | 152 |
| E" (°C.) | 163 | 174 | 151 | 156 | 165 | 168 |
| Tan δ | 155 | 182 | 137 | 143 | 173 | 174 |

Other physical properties were examined using coupons from these same ⅛" thick castings. The results are:

| Physical Properties | | | | | | |
|---|---|---|---|---|---|---|
| | DMBCHA-K | DMBCHA-T | DMMDCHA-K | DMMDCHA-T | PACM-20 | PACM-48 |
| Flexural Strength (psi) | 24000 | 23800 | 22950 | 21400 | 20610 | 20250 |
| Modulus psi × 10**5 | 5.14 | 5.03 | 5.00 | 5.14 | 3.71 | 3.48 |
| Tensile Strength (psi) | 12000 | 7000 | 7035 | 10100 | 11560 | 10590 |
| Modulus psi × 10**5 | 4.00 | 4.08 | 4.43 | 3.54 | 3.58 | 3.25 |
| % Elongation | 4.7 | 2.1 | 4.2 | 3.8 | 7.5 | 6.0 |

Physical property differences between DMBCHA and DMMDCHA are minor except for the lower % elongation noted for the apparently unique thermodynamic equilibrium mixture of DMBCA isomers, the same composition giving the unexpectedly superior thermal performance measured by Tg, E', E" and tan δ.

The novel thermodynamic DMBCHA isomer mixture described above solves the problem of too rapid aliphatic diamine reactivity by sterically hindering the amine function through the presence of the adjacent methyl group and provides unexpectedly superior physical property performance, quite unlike the comparable thermodynamic equilibrium mixture of diamine isomers from DMMDCHA.

What is claimed is:

1. A mixture of bridged bi(cyclohexylamine) isomer derivatives represented by the formula:

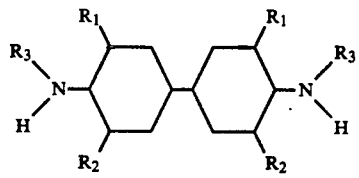

wherein;
$R^1$ is hydrogen or $C_{1-4}$ alkyl;
$R^2$ is $C_{1-4}$ alkyl; and
$R^3$ is hydrogen or $C_{1-4}$ alkyl
and characterized in that at least 50% of the isomers in the mixture are in the trans, trans-isomer configuration.

2. The mixture of bridged bi(cyclohexylamine) isomer derivatives of claim 1 wherein both $R^3$ are hydrogen.

3. The mixture of bridged bi(cyclohexylamine) isomer derivatives of claim 2 wherein at least one $R^2$ is methyl.

4. The mixture of bridged bi(cyclohexylamine) isomer derivatives of claim 3 wherein both $R^1$ are hydrogen.

5. The mixture of bridged bi(cyclohexylamine) isomer derivatives of claim 4 wherein both $R_2$ are methyl.

6. The mixture of bridged bi(cyclohexylamine) isomer derivatives of claim 1 or 2 wherein both $R_2$ are isopropyl.

7. The mixture of bridged bi(cyclohexylamine) isomer derivatives of claim 1 or 2 wherein both $R^2$ are ethyl.

8. The mixture of bridged bi(cyclohexylamine) isomer derivatives of claim 1 wherein both $R^1$ are methyl, both $R^2$ are isopropyl and both $R^3$ are hydrogen.

* * * * *